United States Patent [19]

Picha

[11] Patent Number: 5,706,807
[45] Date of Patent: Jan. 13, 1998

[54] SENSOR DEVICE COVERED WITH FOAM MEMBRANE

[75] Inventor: George J. Picha, Independence, Ohio

[73] Assignee: Applied Medical Research, Garfield Hts., Ohio

[21] Appl. No.: 729,167

[22] Filed: Oct. 11, 1996

Related U.S. Application Data

[62] Division of Ser. No. 364,515, Dec. 27, 1994, Pat. No. 5,564,439, which is a continuation of Ser. No. 128,377, Sep. 28, 1993, abandoned, which is a division of Ser. No. 951,934, Sep. 25, 1992, Pat. No. 5,271,736, which is a continuation of Ser. No. 699,382, May 13, 1991, abandoned.

[51] Int. Cl.$^6$ .................. A61B 5/00; A61B 5/05
[52] U.S. Cl. .................. 128/632; 128/635; 204/403
[58] Field of Search .................. 128/632, 635; 204/403

[56] References Cited

U.S. PATENT DOCUMENTS

| | | |
|---|---|---|
| 3,366,975 | 2/1968 | Pangman . |
| 3,923,939 | 12/1975 | Baker et al. . |
| 4,017,571 | 4/1977 | Rice et al. . |
| 4,034,756 | 7/1977 | Higuchi et al. . |
| 4,340,458 | 7/1982 | Lerner et al. . |
| 4,396,464 | 8/1983 | Giner et al. . |
| 4,531,244 | 7/1985 | Hamas . |
| 4,601,893 | 7/1986 | Cardinal . |
| 4,702,917 | 10/1987 | Schindler . |
| 4,763,658 | 8/1988 | Jones .................. 128/635 |
| 4,889,744 | 12/1989 | Quaid . |
| 4,911,717 | 3/1990 | Gaskill, III . |
| 4,938,218 | 7/1990 | Goodman et al. .......... 128/633 |
| 4,973,320 | 11/1990 | Brenner et al. . |
| 4,976,695 | 12/1990 | Wang . |
| 5,007,929 | 4/1991 | Quaid .................. 623/8 |
| 5,017,624 | 5/1991 | Johnson . |
| 5,026,394 | 6/1991 | Baker . |
| 5,100,392 | 3/1992 | Orth et al. . |
| 5,141,581 | 8/1992 | Markham .................. 623/8 |
| 5,271,736 | 12/1993 | Picha . |
| 5,564,439 | 10/1996 | Picha .................. 623/11 |
| B1 4,889,744 | 3/1993 | Quaid . |

*Primary Examiner*—Paul B. Prebilic
*Attorney, Agent, or Firm*—Pearne, Gordon, McCoy & Granger LLP

[57] ABSTRACT

An implant is provided with an open-celled silicone elastomer foam outer layer. The implant may be formed by compressively deforming beads mixed with liquid elastomer in a mold containing a preformed support structure. The elastomer is cured and the beads dissolved out. Infusion and sensor catheters covered with the foam provide improved transport rates and faster response.

7 Claims, 4 Drawing Sheets

SENSOR DEVICE COVERED WITH FOAM MEMBRANE

This is a division of application Ser. No. 08/364,515, filed on Dec. 27, 1994, and which issued as U.S. Pat. No. 5,564,439 on Oct. 15, 1996, which was filed as a continuation of prior application Ser. No. 08/128,377, filed on Sep. 28, 1993, which application is now abandoned, which was filed as a division of prior application Ser. No. 07/951,934, filed on Sep. 25, 1992, now issued as U.S. Pat. No. 5,271,736, which was filed as a continuation of prior application Ser. No. 07/699,382, filed on May 13, 1991, which application is now abandoned.

BACKGROUND OF THE INVENTION

The present invention relates in general to medical devices, and more particularly to improved biocompatibility for biomedical implants.

Description of the Prior Art

When a foreign object is placed in the soft tissue (fascia, muscle, adipose, etc.) of a living body, it generally attempts to eliminate or isolate the object. Microscopic objects may be engulfed by macrophages and eliminated. Objects which are too large to be engulfed by macrophages tend to be isolated from the body by encapsulation in an envelope of collagen, commonly referred to as a fibrous capsule. Biomedical implants are sufficiently large so as to fall into the latter class and, as foreign objects, are encapsulated by the body in a fibrous capsule.

The fibrous encapsulation of a biomedical implant can lead to certain difficulties. With time, the fibrous capsule can contract, squeezing and deforming the implant. This is a common problem with breast implants. Contraction causes the breast implant to deform and tighten, loosing its natural shape and softness. U.S. Pat. Nos. 3,366,975 and 4,531,244 discuss this problem and solutions thereto. U.S. Pat. No. 3,366,975 also discusses the advantages attendant upon the use of foam in implants. U.S. Pat. No. 5,007,929 shows a method of forming an open-celled silicone elastomer surfaced medical implant and U.S. Pat. No. 4,017,571 shows a method of producing a three dimensional skeletal structure. The teachings of these patents are incorporated herein by reference in their entirety.

It has also been observed that when a fibrous capsule forms, there is a typically diminished vascularity near the implant surface. In the case of drug infusion implants, an increase in vascularity and close proximity or blood vessels to the implant surface is important to provide fast substance exchange between the implant and systemic circulation assuring fast and predictable drug absorption by the body. In the case of sensor implants, increased vascularity and close proximity of vessels to the implant are important to assure fast response times and high sensitivity.

It has been demonstrated that substantial improvement of the vascularization near an implant surface and a reduction in fibrous capsule formation is achieved by presenting the surface morphology of the implant in the form of an array of small, closely-spaced projections. These surface projections interfere with the body's ability to form long, somewhat straight, uniform, strong bundles of collagen fibers, referred to as long-range ordering of collagen, which is disadvantageous since such long-range ordering leads to a capsule more likely to contract and poor vascularity.

Nonetheless, some long-range ordering of collagen occurs in regular arrays of projections because the pathways between the projections are smooth and long. Uninterrupted, straight, canyon-like pathways are present, in which long, somewhat straight collagen bundles can form.

The best response for surfaces having an array of projections occurs within a fatty tissue bed. However, using an implant with an array of projections in fascial tissue frequently results in a fluid accumulation between the base of the implant and the surrounding fibrous capsule. This dead space may compromise the delivery of a drug or the sensing of a desired parameter.

SUMMARY OF THE INVENTION

The present invention provides implants that significantly alter or eliminate capsule formation by disruption in its order. The invention improves the general vascularity about the implant and its proximity to the implant surface in contrast to a smooth surface, as well as improving the fixation of the implant.

The open-celled polymeric foam of the invention allows tissue growth into the interstices of the foam. This promotes vascularity and discourages the formation of long range ordering of collagen bundles running along the implant's surface.

Greater vascularity close to the implant's surface improves the rate at which material can be transferred between the body and the implant. This is important for both the infusion of therapeutic agents and the measuring of bodily parameters with implanted sensors.

The open-celled silicone foam according to the invention is superior to conventionally made foams such as polyester foams which tend to decompose in the body. By controlling the structure of the foam, the degree of fibrosis, hemorrhaging and inflammation can be controlled while retaining good vascularity.

The invention includes a method for making an implant to be implanted into an animal or human being. The method comprises placing a support structure in a mold, placing an uncured polymeric material in the mold, placing deformable beads in the mold, compressing the mold to deform the beads into general mutual contact, curing the polymeric material to bond it to the support structure and to form a solid matrix between the deformed beads, and then removing the deformed beads from the matrix. This provides an implant having a open-celled foam surface formed of the polymeric material.

In the preferred embodiment, the polymeric material has a curing temperature approximately the same as the plastic temperature of the beads. The beads and polymeric material are heated to this temperature during the curing process.

The support structure may be, for example, a permeable or semipermeable membrane surface or a membrane having orifices adapted to allow the passage of a fluid. The membrane with orifices may include pits containing the orifices extending into the foam.

The invention also includes an implant made by the method comprising placing a support structure in a mold, placing an uncured polymeric material in the mold, placing deformable beads in the mold, compressing the mold to deform the beads into general mutual contact, curing the polymeric material to bond it to the support structure and to form a solid matrix between the deformed beads, and removing the deformed beads from the matrix.

The invention also includes an infusion device for infusion of a therapeutic substance into soft tissue. The device includes a receptacle for the therapeutic substance where the receptacle has a therapeutic substance emitting portion. An open-celled polymeric foam between 10 microns and 2,000 microns in thickness covers a substantial portion of the emitting portion.

The emitting portion may comprise a membrane permeable or semipermeable to the therapeutic substance. As an alternative, the emitting portion may be a membrane having orifices. The membrane with orifices may include pits containing the orifices and extending into the foam.

The invention also includes a sensor device for sensing a characteristic of a bodily fluid. The device includes means for sensing the characteristic and a receptacle containing the sensing means where the receptacle has a bodily fluid admitting portion. An open-celled polymeric foam between 10 microns and 2,000 microns in thickness covers a substantial portion of the admitting portion.

The admitting portion may comprise a membrane permeable or semipermeable to the bodily fluid. As an alternative, the admitting portion may be a membrane having orifices. The membrane with orifices may include pits containing the orifices and extending into the foam.

DESCRIPTION OF THE PREFERRED EMBODIMENTS

Figure 1:
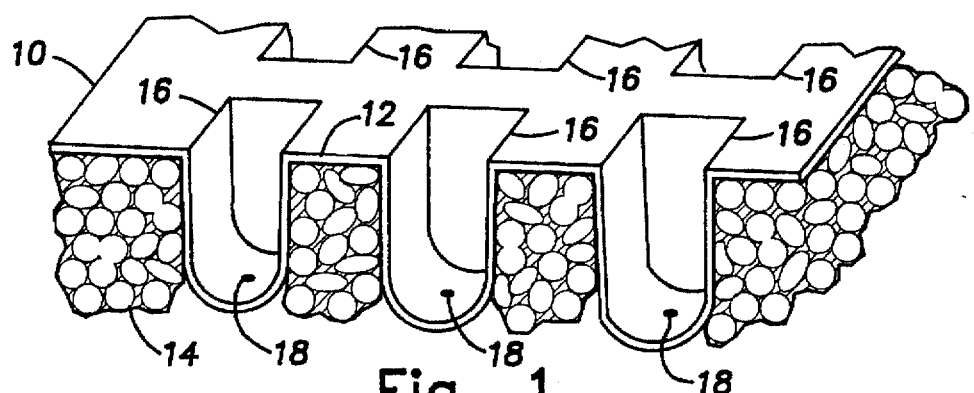
FIG. 1 is a perspective view of a portion of an implant according to the invention.

Referring to FIG. 1, a portion of an implant 10 is shown. A membrane 12 is bonded to a polymeric foam 14. A plurality of pits 16 in the membrane 12 extend into the foam 14. The pits 16 are each provided with an orifice 18. The membrane 12 acts as a support for the foam 14.

In the preferred embodiment, the foam 14 is an open-celled foam or matrix or a bio-compatible silicone elastomer. The foam 14 may be, for example, between 10 and 2,000 microns in thickness and have a nominal cell diameter of 10 microns to 1,000 microns. The foam 14 may also be formed, for example, from a polyurethane or a hydrogel.

The membrane 12 may be, for example, made of a bio-compatible silicone elastomer.

The pits 16 may be, for example, spaced apart between 50 and 2,000 microns, between 50 and 2,000 microns across and as deep as the foam 14 or up to 100 microns beyond the foam 14.

The orifices 18 may be simple holes up to, for example, 250 microns in diameter, down to slits, as appropriate for the rate of fluid flow/exchange desired.

Figure 2:
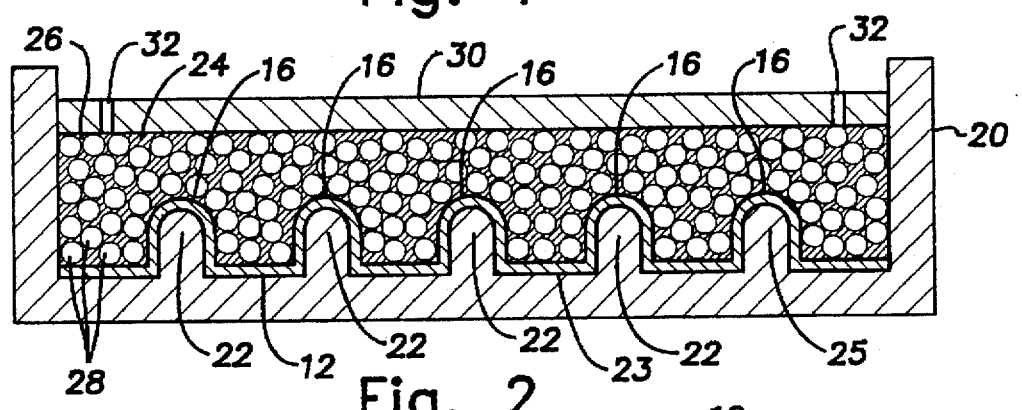
FIG. 2 is a cross sectional view of a mold being used to form the implant according to the invention.

Referring to FIG. 2, a method for making the implant 10 is shown. A mold bottom 20 is provided with projections 22. The membrane 12 may be formed by applying a liquid silicone elastomer or other film over the bottom surface 23 of the mold bottom 20 and curing the membrane 12. The orifices 18 (not shown in FIG. 2) in the pits 16 may be formed at this time or created later (e.g. by piercing or cutting).

A mixture 24 of a polymeric material 26 (e.g. liquid silicone elastomer) and deformable beads 28 is added to the mold bottom 20 on top of the membrane 12. The beads may be, for example, nominally 10 to 1,000 microns in diameter and formed of polyvinyl acetate.

A mold top 30 is used to compress the mixture 24. The beads 28 are pressed into general mutual deformed contact while excess polymeric material 26 is forced out vent holes 32. The beads 28 are deformed to provide substantial contact with one another, the membrane 12 and the mold top 30.

The polymeric material 26 is then cured to form a solid matrix about the beads 28, that is, in the spaces remaining between the beads 28. Because the beads 28 are deformed against one another, the amount of mutual contact, and hence the amount interconnection between the cells of the finished foam, is greatly increased over prior art methods of making medical foams.

In the preferred embodiment, the polymeric material 26 and the beads 28 are chosen such that the curing temperature of the polymeric material 26 is approximately the same as the glass transition or plastic temperature of the beads 28 (e.g. 80 degrees Celsius plus or minus 5 degrees). The mixture 24 is heated to this temperature prior to compressing the pieces of the mold 20, 30. This minimizes the pressure necessary to compress the beads and avoids damage to the membrane 12.

The bead 28 do not interfere with the polymerization or curing process of the polymeric material 26.

After the polymeric material 26 has cured, the beads 28 are removed from the matrix by, for example, dissolving (extracting) the beads 28 in toluene.

Figure 3:
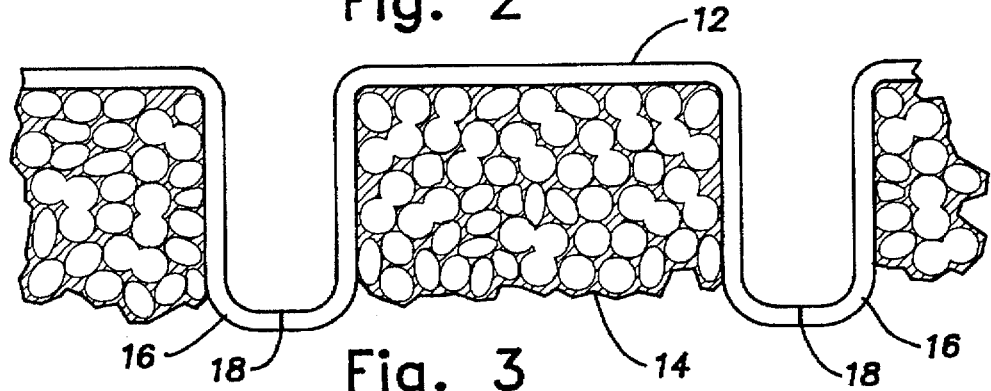
FIG. 3 is a cross sectional view of the implant of FIG. 1.
Figure 4:
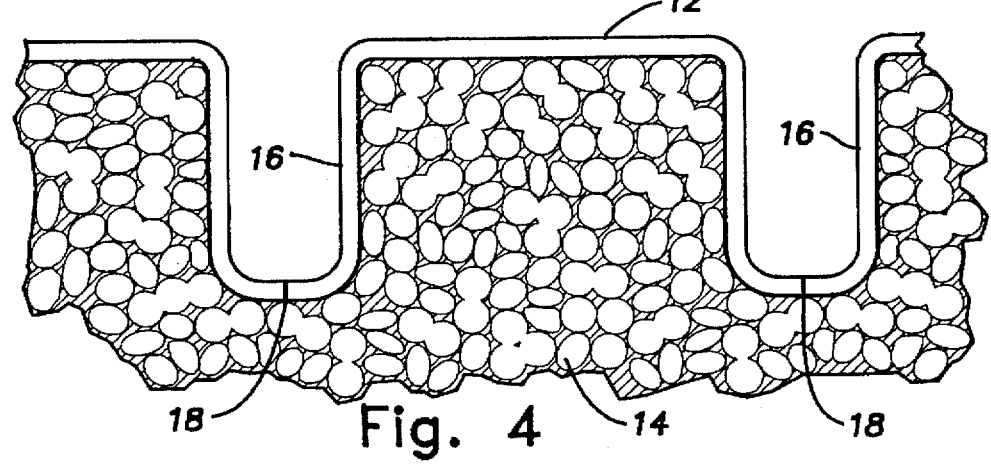
FIG. 4 is a cross sectional view of another embodiment of the invention.

Referring to FIGS. 3 and 4, variations in the thickness of the foam 14 with respect to the depth of the pits 16 are shown. The pits 16 may extend out from the foam 14 as in FIG. 3, or be totally within the foam 14 as in FIG. 4.

The extension of the pits 16 beyond the foam 14 allows direct access to the peri-implant vascularity (e.g. less than 100 microns beyond).

In addition, it is possible to use a foam 14 having a cell diameter substantially less than the dimensions of the pits 16, thereby allowing the pits 16 to just have a thin coating of the foam 14 that follows the general contour of the pits 16.

Figure 5:
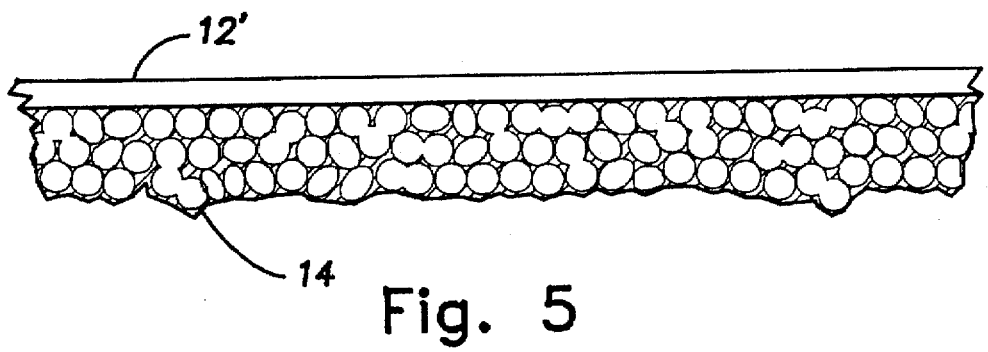
FIG. 5 is a cross sectional view of an additional embodiment of the invention.

Instead of using a membrane 12 having pits 16, it is also possible to use a membrane 12 with no pits (i.e. zero depth pits) but still having orifices 18. Referring to FIG. 5, it is also possible to use a permeable or semipermeable membrane 12' bonded to the foam 14 if appropriate for the rate of fluid flow/exchange desired. A semipermeable membrane excludes some molecular weight species from moving through the membrane.

Figure 6:
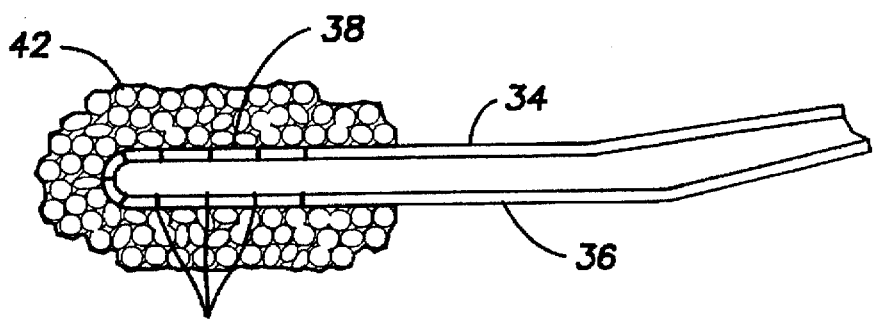
FIG. 6 is a cross sectional view of a catheter according to the invention.

Referring to FIG. 6, a catheter 34 is shown. A tube 36 ends in a receptacle 38 having orifices 40. The outside of the portion 38 is covered by a foam 42 bonded thereto. The tube 36 may be, for example, a silicone elastomer and the foam 42 an open-celled polymeric foam (e.g. silicone elastomer foam).

The foam 42 may have, for example, a depth of 10 to 2,000 microns and the orifices 40 a diameter of 250 microns, down to slits, as appropriate for the rate of fluid flow desired.

The catheter 34 may be inserted into the soft tissue of a human being or animal and the tube 34 connected percutaneously to a source of a therapeutic substance which is then infused out through the orifices 40 and the foam 42. If desired, the receptacle 38 could be replaced by a similar portion without the orifices 40, but made of a material permeable to the therapeutic agent (e.g. a permeable membrane or a semipermeable membrane that passes only molecules having a molecular weight similar to that of the therapeutic agent).

Figure 7:
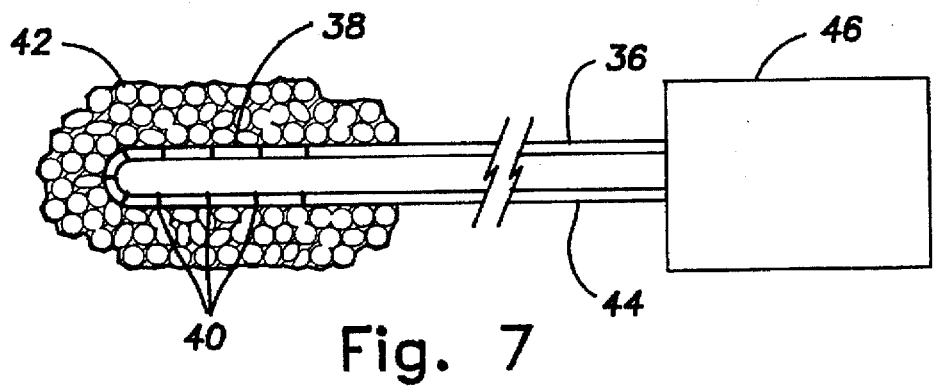
FIG. 7 is a partially cross sectional and partially schematic view of a subcutaneous catheter according to the invention.

Referring to FIG. 7, a catheter 44 similar to that of FIG. 6 is shown. Instead of the tube 36 connecting to a therapeutic substance source outside the body, it connects to a subcutaneous reservoir 46. The reservoir 46 may be, for example, a subcutaneous needle port or a subcutaneous pump. In the case of a needle port, a hypodermic needle is inserted from outside the body into the reservoir 46 and the therapeutic substance injected into the catheter 44 for infusion into the body. Alternatively, the pump (reservoir 46) would provide a controlled amount of the therapeutic substance to the catheter 44.

If desired, the receptacle 38 could be replaced by a similar portion without the orifices 40, but made of a material permeable to the therapeutic agent (e.g. a permeable membrane or a semipermeable membrane that passes only molecules having a molecular weight similar to that of the therapeutic agent).

Figure 8:
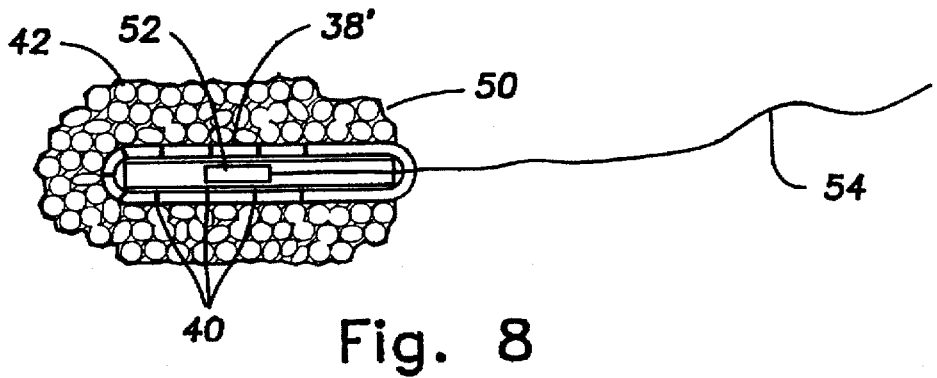
FIG. 8 is a cross sectional view of a sensor device according to the invention.

Referring to FIG. 8, a sensor device 50 is shown. A sensor 52 to measure a characteristic of a bodily fluid (e.g. oxygen, blood sugar, pH, etc.) is contained inside a receptacle 38' having orifices 40. The outside of the receptacle 38' is covered with the foam 42. A wire 54 to the sensor passes through the receptacle 38'.

In operation the sensor 50 is implanted in the soft tissue where the bodily fluid having the characteristic to be sensed is conveniently available. The fluid is admitted through the foam 42, into the orifices 40 and measured by the sensor 52. If desired, the receptacle 38' could be replaced by a similar portion without the orifices 40, but made of a material permeable to the bodily fluid or a semipermeable material that is permeable to some desired constituent of the bodily fluid.

The use of foam on the surface of the described implants may not only minimize the formation of a fibrous capsuled depending on its site of implantation (i.e. fatty tissue be reduces fibrosis), but also enhances the fixation of the implant and increases vascular ingrowth. This is because the foam not only allows the invasion of cells and vascularity, but also promotes continued inflammation and fibrosis.

The inflammation enhances vascularity which improves the mass transport properties of the device by bringing in new blood vessels in number and intimate contact with the surface of the implant. By controlling the structure of the foam, the degree of hemorrhaging and inflammation can be controlled while retaining good vascularity and fibrosis.

Figure 9:
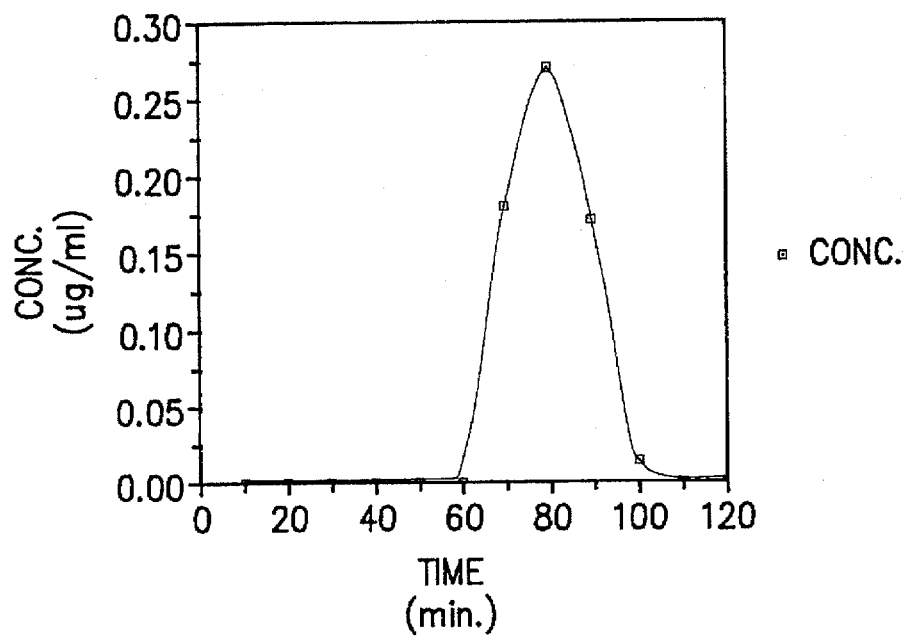
FIG. 9 is a graph of experimentally measured values of concentration with respect to time in a rabbit subcutaneously injected.

Referring to FIG. 9, the blood concentration of a marker dye with respect to time after the dye is injected subcutaneously into a rabbit is shown. The concentration of the dye reaches a maximum blood level concentration after 80 minutes.

Figure 10:
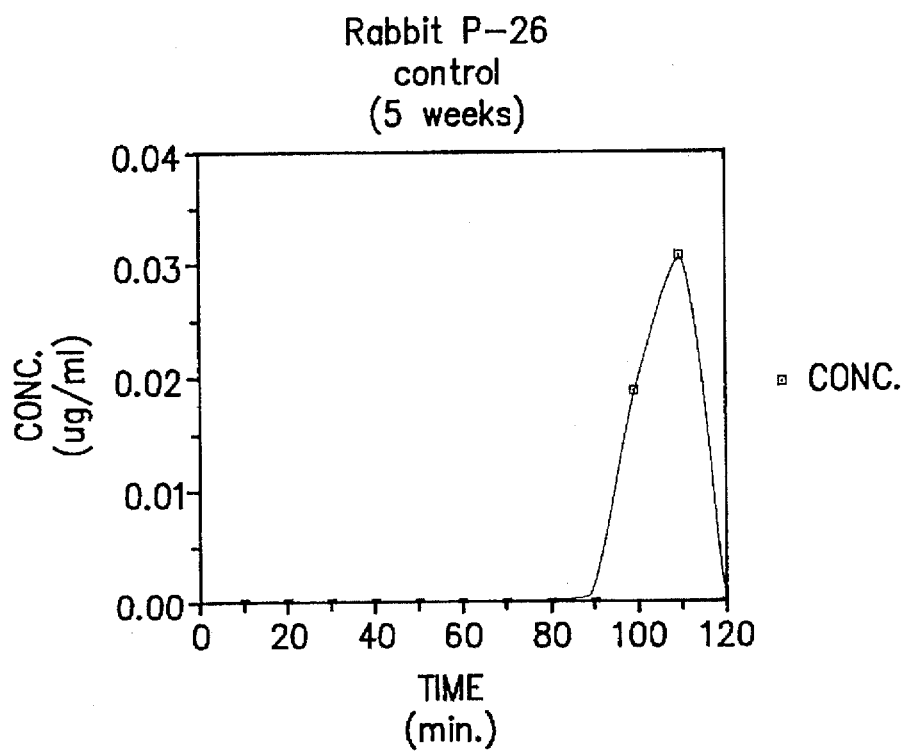
FIG. 10 is a graph of experimentally measured values of concentration with respect to time in a rabbit implanted with a catheter without a foam covering.

Referring to FIG. 10, the blood concentration of a marker dye with respect to time after the dye is injected into a non-foam covered infusion catheter is shown. This is five weeks after subcutaneous implantation of the catheter. The concentration only reaches a little above 0.03 micrograms per milliliter after 110 minutes.

Figure 11:
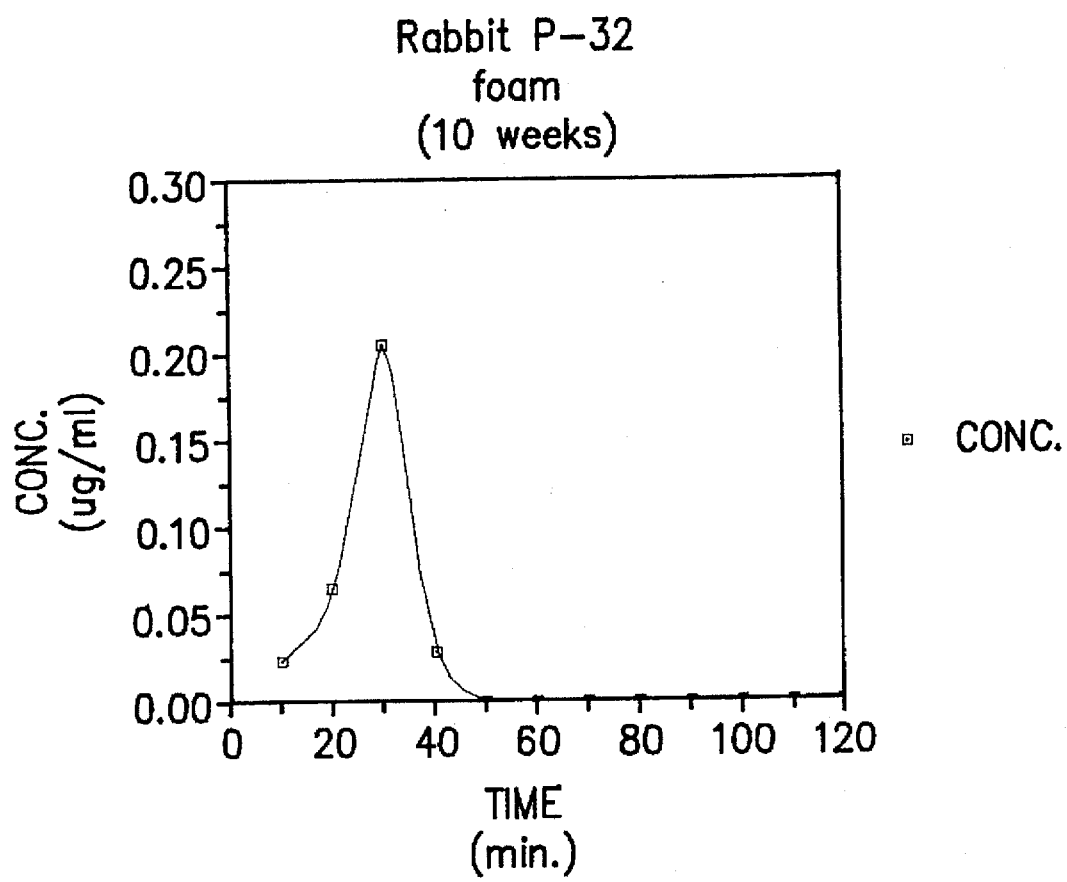
FIG. 11 is a graph of experimentally measured values of concentration with respect to time in a rabbit implanted with a catheter according to the invention.

Referring to FIG. 11, the blood concentration of a marker dye with respect to time after the dye is injected into a foam covered infusion catheter according to the invention is shown. This is ten weeks after subcutaneous implantation of the catheter. The concentration reaches over 0.20 micrograms per milliliter after only 30 minutes.

By using a foam covered catheter according to the invention, the mass transfer rate is comparable to the direct injection, but with a response time over twice as fast as either the non-foam catheter or the injection. Plus, this is after 10 weeks when significant encapsulation would normally have been present, with anticipated degradation in performance.

It should be evident that this disclosure is by way of example and that various changes may be made by adding, modifying or eliminating details without departing from the fair scope of the teaching contained in this disclosure. The invention is therefore not limited to particular details of this disclosure except to the extent that the following claims are necessarily so limited.

What is claimed is:

1. A sensor device for sensing a characteristic of a bodily fluid, said device comprising:

means for sensing said characteristic;

a receptacle containing said sensing means, said receptacle having a bodily fluid admitting membrane; and a polymeric open-celled foam between 10 microns and 2,000 microns in thickness covering a substantial portion of said admitting membrane, said membrane having pits extending at least partially into said foam and at most 100 microns beyond said foam.

2. A sensor device according to claim 1, wherein said foam is a silicone elastomer.

3. A sensor device according to claim 1, wherein said admitting portion comprises a membrane permeable to said bodily fluid or a constituent of said bodily fluid.

4. A sensor device according to claim 1, wherein said admitting portion comprises a membrane having orifices.

5. A sensor device for sensing a characteristic of a bodily fluid, said device comprising:

means for sensing said characteristic;

a receptacle containing said sensing means, said receptacle having a bodily fluid admitting portion having a membrane having orifices; and a polymeric open-celled foam between 10 microns and 2,000 microns in thickness covering a substantial portion of said admitting portion, wherein said membrane has pits extending into said foam, said pits containing said orifices.

6. A sensor device according to claim 5, wherein said foam is a silicone elastomer.

7. A sensor device according to claim 1, wherein said pits are spaced apart between 50 and 2,000 microns and said pits are between 50 and 2,000 microns across.

* * * * *